(12) United States Patent
Moxon et al.

(10) Patent No.: US 8,086,316 B2
(45) Date of Patent: Dec. 27, 2011

(54) WIRELESS CONTROLLED NEUROMODULATION SYSTEM

(75) Inventors: Karen Moxon, Collingswood, NJ (US);
Andrew Khair, Monroeville, NJ (US);
Michael Darling, Trenton, NJ (US);
Ebraheem Sultan, Shuwaikh (KW)

(73) Assignee: Drexel University, Philadelphia, PA (US)

( * ) Notice: Subject to any disclaimer, the term of this patent is extended or adjusted under 35 U.S.C. 154(b) by 378 days.

(21) Appl. No.: 11/753,256

(22) Filed: May 24, 2007

(65) Prior Publication Data
US 2007/0282389 A1 Dec. 6, 2007

Related U.S. Application Data

(60) Provisional application No. 60/803,076, filed on May 24, 2006.

(51) Int. Cl.
*A61N 1/00* (2006.01)
(52) U.S. Cl. ............... 607/45; 607/2; 607/116
(58) Field of Classification Search ............ 607/45, 607/59, 116, 118, 46
See application file for complete search history.

(56) References Cited

U.S. PATENT DOCUMENTS

| | | | |
|---|---|---|---|
| 6,134,474 A * | 10/2000 | Fischell et al. | 607/45 |
| 6,289,237 B1 | 9/2001 | Mickle et al. | |
| 6,337,997 B1 * | 1/2002 | Rise | 607/45 |
| 6,658,287 B1 * | 12/2003 | Litt et al. | 600/544 |
| 6,834,200 B2 | 12/2004 | Moxon et al. | |
| 2005/0090756 A1 * | 4/2005 | Wolf et al. | 600/546 |

* cited by examiner

*Primary Examiner* — Carl H Layno
*Assistant Examiner* — Pamela M Bays
(74) *Attorney, Agent, or Firm* — Riverside Law LLP

(57) ABSTRACT

An apparatus is disclosed for controlled neuromodulation. The apparatus includes a plurality of neural sensors, wherein each of the neural sensors is electrically connected to a separate signal conditioner. Each of the signal conditioners produces a neural sensor signal, which is analyzed by a separate threshold detector to produces a neural event signal when the neural sensor signal exceeds a threshold level associated with the threshold detector. Each of the threshold detectors is connected to a wireless transceiver and the wireless transceivers transmit the neural event signals to a processor. The processor analyzes the neural event signals and determines the presence or absence of a clinical brain state. The apparatus can be used to detect and control epileptic seizures.

11 Claims, 5 Drawing Sheets

WIRELESS CONTROLLED NEUROMODULATION SYSTEM

CROSS-REFERENCE TO RELATED APPLICATIONS

This utility application claims the benefit under 35 U.S.C. §119(e) of Provisional Application Ser. No. 60/803,076 filed on May 24, 2006 entitled WIRELESS MULTI CHANNEL NEURAL SIGNAL PROCESSING DEVICE AND METHOD, the entire disclosure of which is incorporated by reference herein.

BACKGROUND OF INVENTION

Epilepsy affects between 0.5 to 1.0% of the general U.S. population, or well over 2 million people. Approximately 20% of these patients do not respond to the best available treatments and continue to have intractable seizures. The economic effect of these numbers and the overall burden to the U.S. health care system is staggering. Epilepsy management translates to annual financial costs of approximately $12.5 billion. The indirect employment related costs are more substantial and they are based on a survey of about 1200 patients in 18 centers. It is estimated that there is a loss of lifetime earnings of 35% in men and 25% in women. Of the new cases diagnosed every year, 61% have no further seizures after the first year and so their overall costs fell drastically after the initial evaluation. 14% had seizures for a year or two, but then eventually became seizure-free for a whole year. Over 20% of new patients never responded well to treatment and continued to have seizures. Due to the addition of new cases in excess of 0.5 million people with epilepsy are not controlled and continue to have seizures. This emphasizes the importance of seizure detection and control and its relationship to the total medical costs.

Of alternative treatments only brain surgery and vagus nerve stimulator (VNS) are significant. The former treatment option can offer a 50-65% probability of freedom from disabling seizures but is possible in only 8% of patients who continue to have seizures. Brain imaging, EEG and exam provide good prognostic information if surgery is likely to be successful, for example in the case of an accessible brain tumor the outcome is usually good. The option of a seizure detection and control device offers a valuable alternative to surgical treatment since surgery can not be performed in cases of epileptic lesions localized to vital, or "eloquent", brain areas and it also offers the possibility of empirical treatment with less need to verify that seizures originate in a certain brain lesion. VNS offers only palliative treatment in the best of cases. A third alternative treatment, antiepileptic drugs (AED), is complicated by both short-term and long-term side effects. Among the former are psychomotor slowing and decreased cognition, sleepiness and gait disorders. Long term side effects are well known in the older AED probably these have been on the market for a long enough time that they have been detected and the include: osteoporosis, neuropathies, cerebellar atrophy, retinal damage, liver, pancreas and bone marrow problems. Moreover, these drugs are not recommended for women of child bearing age. An improved seizure detection and control device will eliminate the side effects of drug therapy and make productive, those patients who do not respond to alternative treatments. In addition to these possible beneficial effects an improved seizure detection and control would provide improvement of secondary effects of seizures, like depression and psychosis that affects a majority of patients with epilepsy.

An approach to seizure control is to detect the early onset of a seizure and apply either a drug or electrical stimulus to prevent the imminent seizure. Many studies have been done to attempt to detect the onset of seizures using data recorded from EEG electrodes, which are placed on the skin and are, therefore, non-invasive. These methods have generally failed because the information recorded by EEG electrodes has generally been degraded in space and time because the electrodes are placed on the surface of the skin. While it has been demonstrated that seizures can be predicted using pre-seizure neural data from EEG electrodes, the methods are not very accurate and generally a solution can not be computed in real-time. Computing the solution can take hours to days, by which time the seizure has already occurred.

Recently, it has been shown that imminence of seizure can be detected by measurement and analysis of multiple single neuron action potentials. See Moxon, et al. "Real-time Seizure Detection System using Multiple Single Neuron Recordings," Proceedings of the 23rd Annual International Conference of the IEEE Engineering in Medicine and Biology Society, Istanbul, Turkey, Oct. 25-28, 2001. (Attached as Appendix A). This article and all other references cited in this application are incorporated by reference as if fully set forth herein. When the correlation between neurons recorded on different sites reaches a critical level, a seizure is imminent. At this point, microstimulation or drug administration can be triggered to prevent the full seizure.

For severe cases of epilepsy, implantable microelectrode devices can accurately detect seizure onset in real-time and report on the state of the future seizures giving time for the patient to react or to implement a strategy to stop the onset of the seizure. For these patients an implantable device is warranted because of the severity of the disease. Since this method requires implanting intracranial electrodes, the method is only appropriate for those patients for which other methods do not work. As stated above, this represents about 20% of the total epilepsy patient population or about 500,000 total patients at the present time.

Implantable stimulating microelectrodes are used frequently and have proven very effective in controlling late stages of Parkinson's disease. Methods are currently being pursued to implant microelectrodes for obesity, depression and various dyskinetic disorders. Recently a quadriplegic spinal cord patient was implanted with microelectrodes to record single neurons to restore motor output from the brain.

Recording single neuron action potentials, or spikes, from the brain is generally performed using an array of microelectrodes. In the past, cables have been used to transmit the analog signals from the microelectrodes to a waveform discriminator that detects a spike and registers the spike time. This cabling system requires that the subject be tethered and this tethering limits the movement of the subject and may cause recording disturbance.

A need exists for an effective seizure detection and control system wherein implanted microelectrodes connect to a device that discriminates single neuron spikes, identifies the spike times and transmits this information telemetrically to a controller that analyzes the spikes, determines whether a seizure is imminent and triggers a stimulus or drug to prevent the seizure. Such a device has applicability not only to epilepsy, but to any other area of controlled neuromodulation.

SUMMARY OF INVENTION

An apparatus is disclosed for controlled neuromodulation. The apparatus includes a plurality of neural sensors, wherein each of the neural sensors is electrically connected to a separate signal conditioner for each signal channel on the neural sensor. Each of the signal conditioners produces a neural sensor signal, which is analyzed by a separate threshold detector to produce a neural event signal when the neural sensor signal exceeds a threshold level associated with the threshold detector. Each of the threshold detectors is connected to a wireless transceiver and the wireless transceivers transmit the neural event signals to a processor. The processor analyzes the neural event signals and determines the presence or absence of a clinical brain state.

In a further embodiment, the apparatus includes a neuron stimulator or a drug delivery device and the processor activates the neuron stimulator or the drug delivery device upon a determination that the clinical brain state exists. In a further embodiment, the apparatus can be used to detect and control epileptic seizures. In a further embodiment, the neural sensors can be part of a multi-site electrode. In a further embodiment, the threshold level associated with each threshold detector is adjustable. In a further embodiment, the threshold levels can be externally adjusted by the processor via the wireless transmitters. In a further embodiment, the determination of a clinical brain state is based on a correlation measurement of the neural event signals.

A method is also disclosed for controlling epileptic seizures in a human or an animal. The method includes the steps of: sensing the single neuron activity in the brain of the human or animal with neural sensors; determining for each neural sensor when the neural activity is above a threshold that indicates that the neuron has fired an action potential; wirelessly transmitting information relating to the determination that the neuron has fired an action potential to a monitoring processor; and correlating the transmitted information to determine when a seizure is imminent and initiating a stimulus to prevent the seizure from occurring.

In another embodiment, a method for monitoring neural signals is disclosed. The method includes the steps of: placing an electrode in the vicinity of a neuron to be monitored; measuring a voltage signal created at the electrode by the neuron to be monitored; detecting when the voltage signal reaches a threshold that indicated that the neuron has fired an action potential. The method can also include the additional step of storing a record of when the neural action threshold occurred.

BRIEF DESCRIPTION OF SEVERAL VIEWS OF THE DRAWINGS

The foregoing summary, as well as the following detailed description of the invention, will be better understood when read in conjunction with the appended drawings. For the purpose of illustrating the invention, there are shown in the drawings certain embodiments which are presently preferred. It should be understood, however, that the invention is not limited to the precise arrangements and instrumentalities shown.

DETAILED DESCRIPTION OF THE INVENTION

Figure 1:
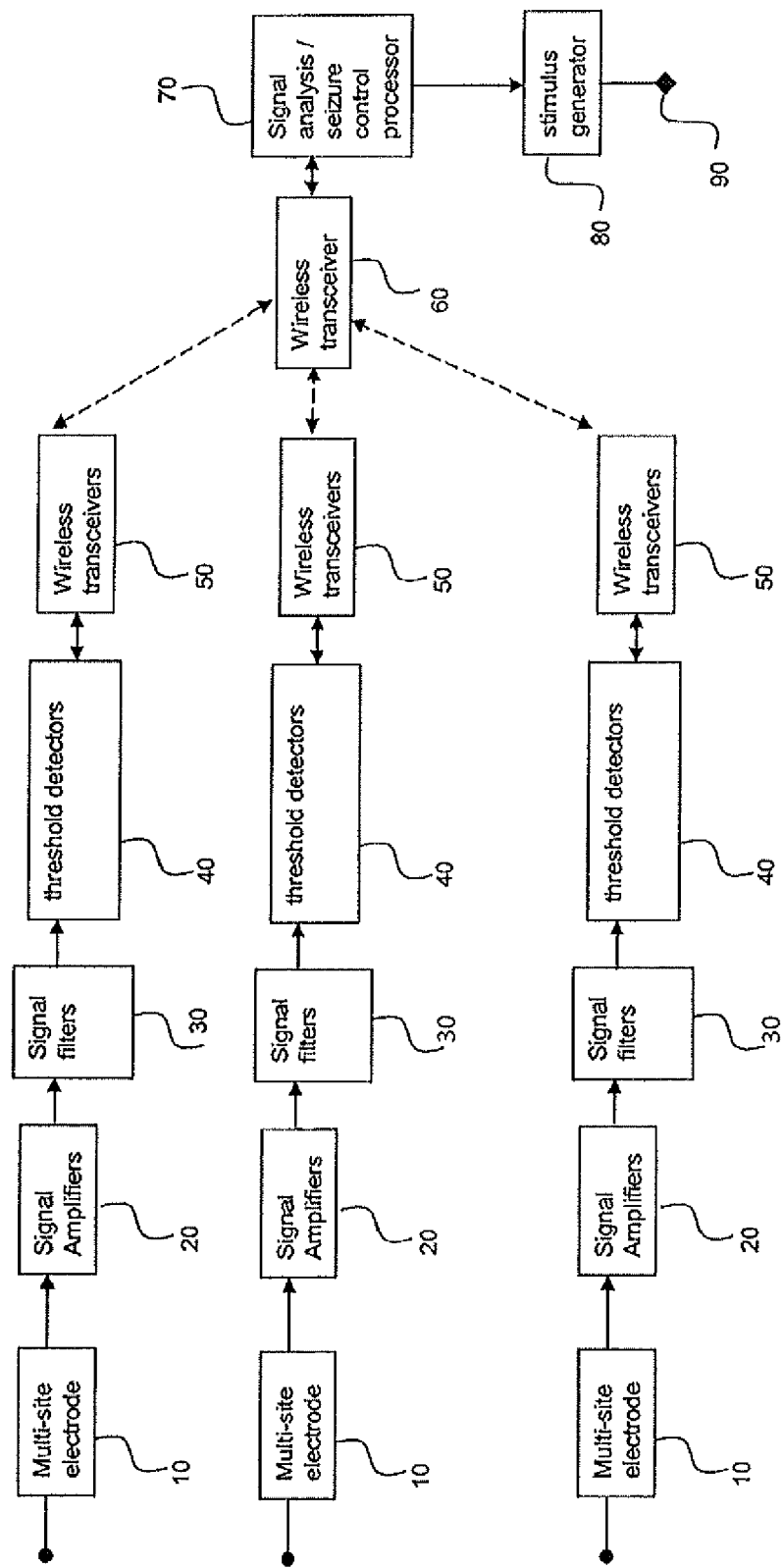
FIG. 1 is an exemplary design block diagram of a wireless real-time controlled neuromodulation system.

Referring now to various figures of the drawings wherein like reference characters refer to like parts, there is shown in FIG. 1, a block diagram of an exemplary embodiment of an apparatus for detection and control of epileptic seizures.

Microelectrodes 10 are inserted in the brain of a human or animal to sense neural activity at a plurality of sites. In an exemplary embodiment, multiple microelectrodes are combined on ceramic based multi-site electrodes such as those described in U.S. Pat. No. 6,834,200 (Moxon et. al) Ceramic Based Multi-site Electrode Arrays and Methods for Their Production. Each of the microelectrodes is connected to a signal amplifier 20, one for each electrode site. One skilled in the art will recognize that the gain and input impedance of the signal amplifier should be suitable for the voltage generated by the microelectrode 10 when receiving a neural signal. An exemplary signal amplifier is disclosed in provisional application No. 60/803,076, referenced above and incorporated herein by reference. In an exemplary embodiment, the signal from the signal amplifier is filtered with a signal filter 30, which limits the frequency response of the signal from the microelectrode to eliminate unwanted noise, which may be generated from external sources. The filtered signal from the signal filter is then processed by a threshold detector 40. The threshold detector 40 detects when the amplified and filtered signal from the microelectrode 10 has reached a predetermined voltage level. One purpose for the threshold detector is to limit the amount of information transmitted to the analysis and control processor 70 via the wireless transceiver 50. Since the neural signal is to be transmitted via a wireless transceiver 50, it is desirable to limit the amount of information to be transmitted, thus reducing the bandwidth and power requirements for the wireless transceiver 50. The threshold detector 40 eliminates the need to transmit all of the information contained in a continuous analog neural signal waveform and limits this information to a discrete indication of when the neural signal has reached a predetermined voltage level that represents when the recorded neuron fired an action potential. In an exemplary embodiment, the threshold detector is a simple level detector connected to a "one shot" pulse generator, such that a digital pulse is transmitted each time the neural signal crosses the threshold. In another embodiment, the threshold detector can be an embedded processor with an analog to digital converter that measures the neural signal. The embedded processor can send to the wireless transceiver 50 a time stamp when a neural signal has crossed a threshold.

Regardless of the form that the threshold detector 40 takes, in an exemplary embodiment, as shown in FIG. 1, each micro electrode 10 has its own signal amplifier 20, signal filter 30 and threshold detector 40. Further, each threshold detector 40 is connected to a single wireless transceiver 50. In an exemplary embodiment, each sensor/amplifier/threshold detector/transceiver device is powered by a small, long life battery. In a further embodiment, each device has a micro antenna and power supply that is powered by an external radio frequency or other high frequency signal. An example of devices powered in this way is disclosed in U.S. Pat. No. 6,289,237 to Mickel et al. In a further embodiment, a battery or other power supply is embedded in the human or animal at a place remote from the location of the microelectrode 10, signal amplifier 20, signal filter 30, threshold detector 40 and wireless transceiver 50.

The data from the threshold detectors 40 indicating when neural signals have reached predetermined thresholds is transmitted by each wireless transceiver 50 to a wireless transceiver 60 that is connected to a signal analysis processor 70. In an exemplary embodiment, the signal analysis processor 70 is a personal computer and the wireless transceiver is a USB or other device readily adapted for connection to a personal computer. One skilled in the art will recognize that various embodiments are possible for the actual data format and modulation scheme for the wireless transmission of data from the threshold detectors 40 to the processor 70. For example, each wireless transceiver 50 can transmit on a different frequency. In another embodiment, data transmission can be by Code Division Multiple Access or Time Division Multiple Access.

The signal analysis processor 70 implements a predetermined analysis algorithm to analyze the neural signals to determine whether a clinical state under investigation exists or is imminent. For example, it has been demonstrated that analysis of neural signals can predict the onset of an epileptic seizure.

Figure 5:
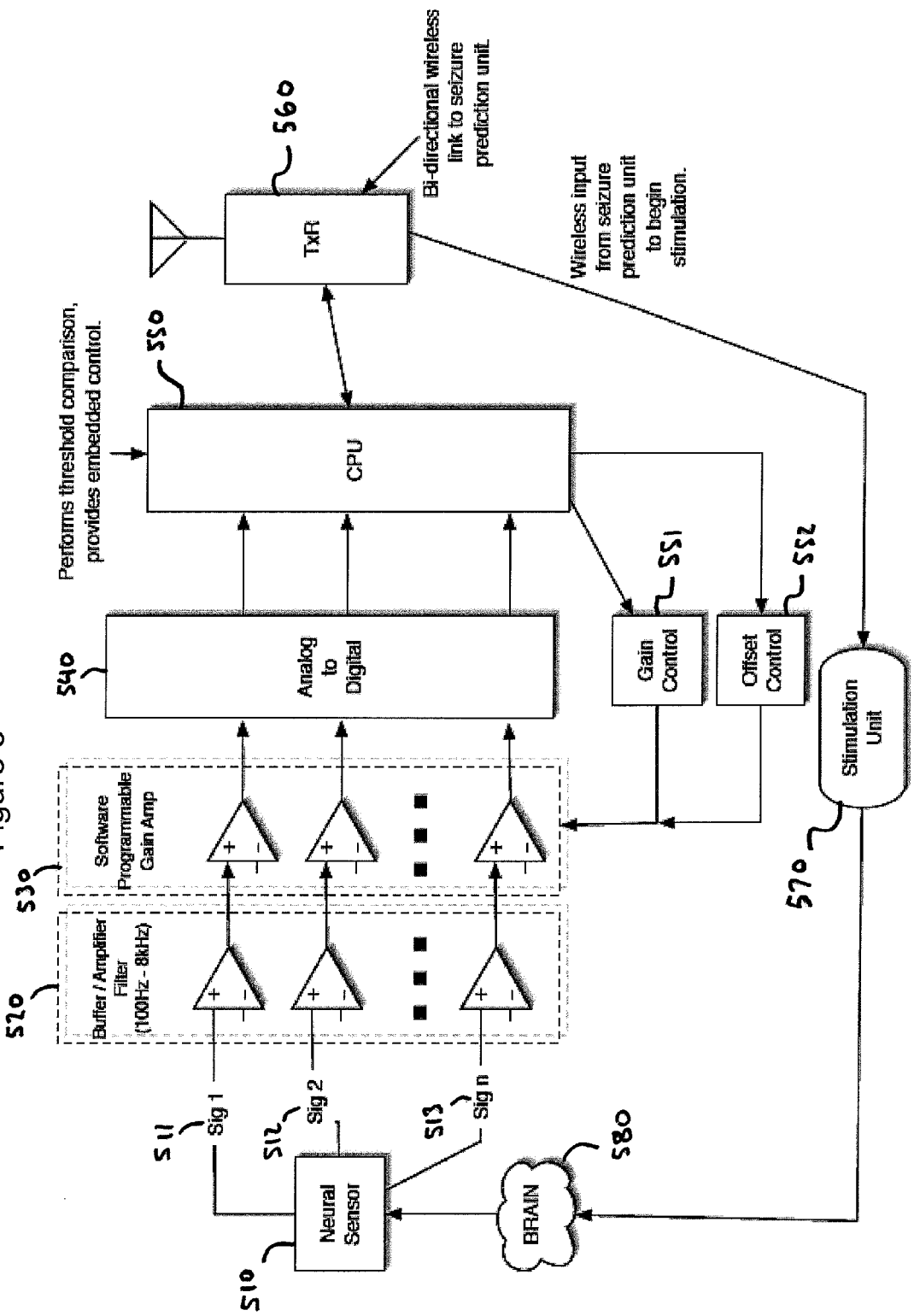
FIG. 5 is an exemplary block diagram of a wireless real-time controlled neuromodulation system.

FIG. 5 is a schematic block diagram of an alternate embodiment of a system for wireless controlled neuromodulation. In this embodiment, a neural sensor 510 installed in a patient's brain 580 contains multiple microelectrodes, each of which produces a separate signal 511-513. The signals 511-513 are amplified by buffer-amplifiers, which can be in a circuit containing multiple such amplifiers 520. The signals from the buffer-amplifiers 520 are then further amplified by a software programmable gain amplifier, which can also be in a circuit containing multiple such amplifiers 530. Each of the signals is then converted from an analog signal to a digital signal by an analog to digital converter 540. The analog to digital converter can have an input multiplexer (not shown) to accommodate multiple input signals 511-513, or can contain several distinct analog to digital converters, or can be distinct individual devices. The analog to digital converter is controlled by a microcontroller 550, which receives the digital versions of the neural signals. The microcontroller 550 determines when each individual neural signal 511-513 goes above a predetermined threshold. The microprocessor 550 sends information indicating when each neural signal exceeds the threshold to a wireless transceiver 560. The wireless transceiver 560 sends this information to an analysis and control processor (not shown) as described above for FIG. 1. In an embodiment, the microcontroller 550 also controls amplifier gain 551 and DC voltage offset 552. The wireless transceiver 560 can receive a signal from the analysis and control processor to initiate a stimulation control signal to a stimulation unit 570. The stimulation unit can deliver a drug or an electrical signal or both. The stimulation unit 570 can be in direct communication with the patient's brain 580, or can cause a drug or electrical stimulus to be applied elsewhere on the patient's body.

In an experiment detailed in Moxon et al., "Real-time Seizure Detection System using Multiple Single Neuron Recordings," Proceedings of the 23rd Annual International Conference of the IEEE Engineering in Medicine and Biology Society, Istanbul, Turkey, Oct. 25-28, 2001, two rats were implanted with an eight channel electrode array to record single-neuron activity. The electrodes were implanted bilaterally into the temporal lobe of each rat. Recordings were made throughout the implantation process to access electrode function. Small screws in the skull were used to anchor the electrodes, which were then cemented into place creating an electrode cap.

After two weeks, the rats were placed in a recording chamber and a headstage was connected to the electrode cap. The headstage transmitted neural signals from the rat to a Multi-Neuron data Acquisition Program (MNAP) that filtered and amplified the signal and discriminated single neuron action potentials from the analog signal. The times of occurrence of action potentials for each neuron were stored.

During a recording session, five minutes of baseline data were collected and then the rats were given an injection of PTZ (40 mg/kg). This dose of PTZ induced generalized seizure activity for up to 3 hours. Continuous recording were made during the 3 hours post-injection.

The raw data from the MNAP system consisted of M channels where M is the number of single neurons recorded per session. Data were represented at one millisecond (1 ms) time intervals and the occurrence of an action potential during that millisecond was represented as a 1. otherwise it was a zero. The seizure detection unit summed the binary data over a 50 msec interval to create a single bin whose value represented the number of times the cell fired an action potential during that 50 ms interval. A window was created that collected 128 bins, representing 6.4 seconds of data for each channel.

Figure 2:
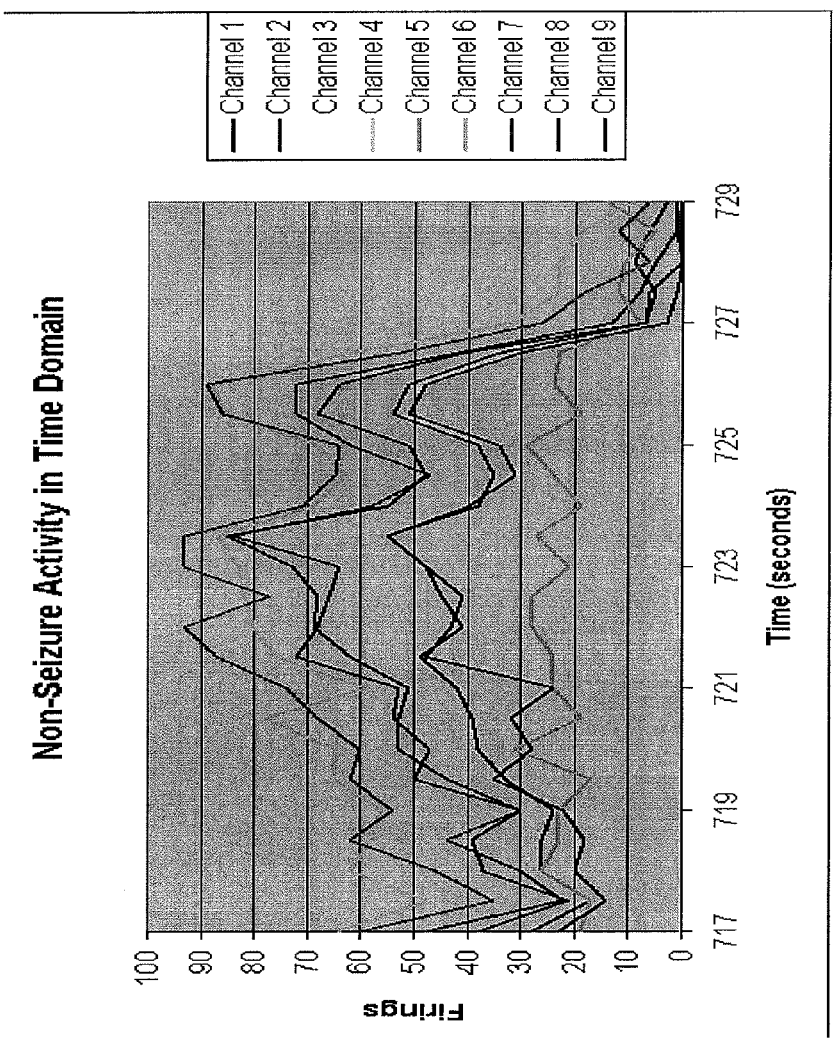
FIG. 2 is an exemplary chart of normal neuron firings.
Figure 3:
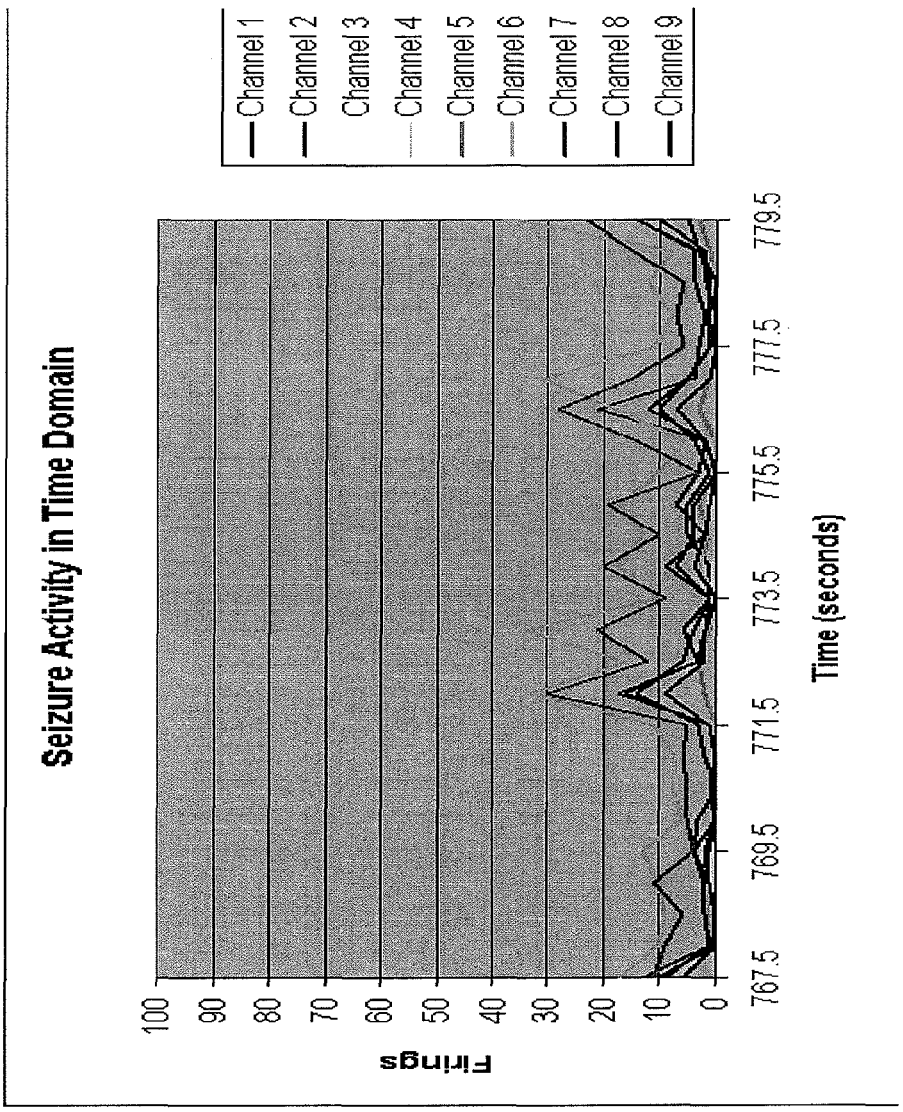
FIG. 3 is an exemplary chart of neuron firings during seizure activity.
Figure 4:
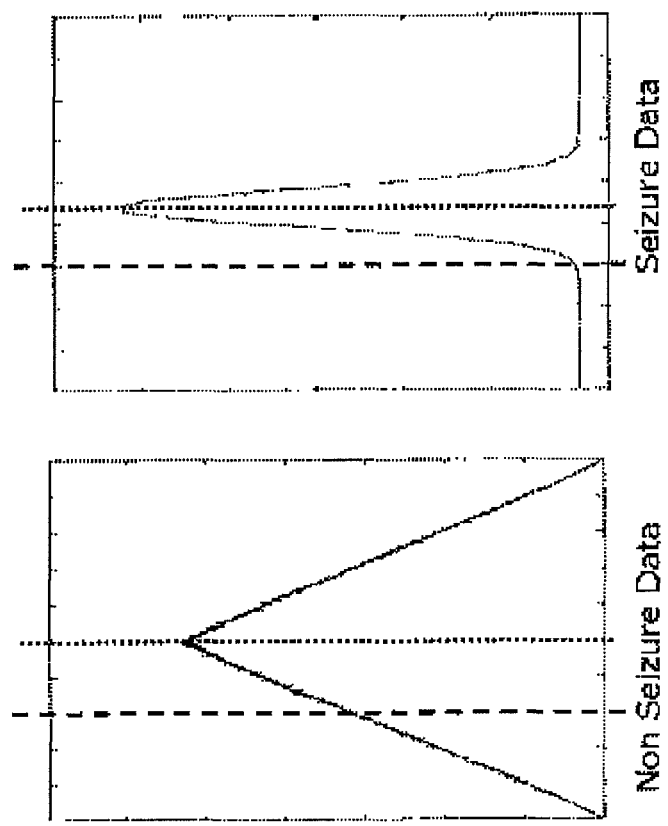
FIG. 4 is an exemplary chart of non-seizure correlation data; and an exemplary chart of seizure correlation data.

Shown in FIG. 2 is an exemplary chart of normal neuron firings. Shown in FIG. 3 is an exemplary chart of neuron firings during seizure activity and FIG. 4 shows exemplary chart of correlation data for normal neuron firings (left side) and during seizure activity (right side). As can be seen in these figures, the neural signals taken collectively are markedly different between non-seizure and seizure conditions, and can be used to predict seizures.

The M windows, one for each neuron recorded, were pairwise cross correlated to create M choose 2 cross-correlation vectors. The cross correlation vectors were created by holding the window for the reference neuron stationary while sliding each of the 128 bins of the window of the correlating neuron past the reference window one bin at a time. For each t, $-127<t<128$, the value of each bin in the reference window is multiplied by the adjacent window of the correlating neuron window. Then t was incremented and the correlating neuron window shifted one bin over the reference neuron window. The process was repeated until the correlated window had moved completely past the reference neuron window. For each bin of the reference window, the product of the reference bins and the correlation bin are added to the result from previous calculation resulting in a correlation vector with length 2t, t=128. The correlation vector for all pair wise correlation were averaged and the standard deviation at t=0 was used as a measure of synchrony. This synchrony measure was used to determine if a seizure was about to occur. See FIG. 4, which is a diagram showing changes in the shape of the correlation function during non-seizure events and during seizure events. The dotted line is the peak of the correlation (representing time 0) while the dotted line represents one standard deviation away from the mean. The value of the correlation function one standard deviation away from the mean was used to determine whether seizure activity was present.

When the value of the standard deviation for each bin was plotted, there was a clear separation between synchrony measures during seizure and nonseizure activity. A critical value for the synchrony measure was selected so that 100% of the seizures had a standard deviation less than this critical value and only 0.3% of the non-seizure bins had a standard deviation less than this critical value. When the standard deviation reached the critical value, 100% of the bins that occurred during the seizure had a standard deviation below this value while 99.7% of the bins recording during the baseline period were above this value. By using this critical value as a cut-off for evaluating the state of the animal, 100% of the seizures were detected and only 0.3% of the non-seizure bins were incorrectly labeled as seizures.

This synchrony was also shown to predict seizures. The continuous data recorded during sessions when the animal had been injected with PZT was streamed into the detection algorithm. The cross-correlation was recomputed for each new 50 msec bin acquired. Under these conditions, not only was the system able to detect 100% of the seizure episodes, but the system also registered a period of synchrony just prior to the seizure onset. This synchrony created a standard deviation of the cross-correlation below the critical value, suggesting a seizure was taking place. However, the standard deviation of the cross-correlation was actually below the critical value approximately 4.6 seconds before the onset of the seizure. These results suggest that this synchrony measure could be used to predict the onset of a seizure.

The procedure outlined here represents a viable method for detecting neural activity associated with the onset of a seizure so that subsequent neural stimulation or drug delivery can be implemented to prevent the seizure onset.

In an exemplary embodiment as shown in FIG. 1, once the signal analysis processor 70 determines that a seizure is imminent, the processor can initiate a stimulus, either a drug delivery or electrical stimulus to forestall the seizure.

The example given above is not meant to limit the scope of the invention to only detection and correction of epileptic seizures. The embodiments described herein can be adapted to detect any brain state that can be discerned by analysis of multiple single neuron signals. Likewise, any mode of stimulus or drug delivery that is responsive to or corrective of a clinical brain state can be initiated once a processor determines the existence of that state.

In further embodiments, the threshold detectors 40 are adapted to allow the threshold to be set by the signal analysis processor 70 or other external means via a signal received by the wireless transceiver 50, which can be a two-way transceiver, that can both transmit neural signal information and receive threshold setting information.

In further embodiments, the stimulus generator 80 is either worn by or implanted in a patient. The signal to initiate a stimulus from the signal analysis processor 70 can be transmitted to the stimulus generator via a wireless link, and the stimulus generator can be battery powered or have any other remote form of power, thus completely freeing the patient from and tethers to the analysis computer.

Without further elaboration, the foregoing will so fully illustrate this invention that others may, by applying current or future knowledge, readily adopt the same for use under various conditions of service.

What is claimed is:

1. An apparatus for controlled neuromodulation comprising:
   a plurality of neural sensors, each neural sensor detecting one or more single neural action potentials;
   a plurality of signal conditioners corresponding on a one-to-one basis with each of said neural sensors, wherein each of said neural sensors is electrically connected to a separate corresponding signal conditioner, each of said signal conditioners producing a neural sensor signal;
   a plurality of threshold detectors corresponding on a one-to-one basis with each of said signal conditioners, wherein each of said neural sensor signals is separately analyzed by a corresponding threshold detector that produces a neural event signal when said neural sensor signals exceeds a threshold level associated with said corresponding threshold detector;
   a plurality of wireless transceivers corresponding on a one-to-one basis with each of said threshold detectors, each of said threshold detectors being connected to a corresponding wireless transceiver; and
   a processor, wherein each of said wireless transceivers transmits each of said neural event signals to said processor which receives all of said neural event signals and determines the presence or absence of a clinical brain state.

2. The apparatus of claim 1, wherein said clinical brain state is an epileptic seizure.

3. The apparatus of claim 1, further comprising a neuron stimulator, wherein said processor activates said neuron stimulator upon a determination that said clinical brain state exists.

4. The apparatus of claim 3, wherein said clinical brain state is an epileptic seizure.

5. The apparatus of claim 1, further comprising a drug delivery device, wherein said processor activates said drug delivery device to deliver a drug to prevent an epileptic seizure upon a determination that said clinical brain state exists.

6. The apparatus of claim 5, wherein said clinical brain state is an epileptic seizure.

7. The apparatus of claim 1, wherein at least one of said neural sensors is placed in the brain of a human or an animal.

8. The apparatus of claim 1, wherein at least two of said neural sensors are part of a multi-site electrode.

9. The apparatus of claim 1, wherein said threshold level associated with each of said threshold detectors is adjustable.

10. The apparatus of claim 9, wherein said processor adjusts said threshold level via one or more of said wireless transceivers.

11. The apparatus of claim 1, wherein said determination is based on a correlation measurement of said neural event signals.

* * * * *